(12) United States Patent
Whickman et al.

(10) Patent No.: US 10,221,209 B2
(45) Date of Patent: Mar. 5, 2019

(54) METHOD AND SYSTEM FOR POLYPEPTIDE PURIFICATION

(71) Applicant: Lonza Biologics PLC, Slough (GB)

(72) Inventors: Mark R. Whickman, High Wycombe (GB); Sam Mansoor, Maidenhead (GB)

(73) Assignee: Lonza Biologics PLC, Slough (GB)

( * ) Notice: Subject to any disclaimer, the term of this patent is extended or adjusted under 35 U.S.C. 154(b) by 530 days.

(21) Appl. No.: 14/525,561

(22) Filed: Oct. 28, 2014

(65) Prior Publication Data

US 2015/0105542 A1  Apr. 16, 2015

Related U.S. Application Data

(62) Division of application No. 13/394,560, filed as application No. PCT/EP2010/063295 on Sep. 10, 2010, now Pat. No. 8,906,231.

(30) Foreign Application Priority Data

Sep. 10, 2009  (EP) .................................. 09169911

(51) Int. Cl.
C07K 1/16 (2006.01)
C07K 1/34 (2006.01)
(Continued)

(52) U.S. Cl.
CPC .............. C07K 1/16 (2013.01); B01D 15/08 (2013.01); B01D 61/16 (2013.01); C07K 1/34 (2013.01);
(Continued)

(58) Field of Classification Search
CPC ........ G01N 30/00; G01N 30/02; G01N 30/48; G01N 30/482; G01N 2030/022; G01N 2030/027; G01N 2030/484; G01N 2030/8804; G01N 2030/8827; G01N 2030/8831; G01N 2030/8881; G01N 33/68; G01N 33/6803; G01N 35/00584; G01N 2035/00475; G01N 2035/00485; C07K 1/02; C07K 1/16; C07K 1/165;
(Continued)

(56) References Cited

U.S. PATENT DOCUMENTS 4,671,870 A  6/1987 Tompa et al.
4,721,572 A  1/1988 Jordan
(Continued)

FOREIGN PATENT DOCUMENTS

CN  85107875 A  4/1987
EP  0176299 A2  4/1986
(Continued)

OTHER PUBLICATIONS

Aldington et al., Scale-up of monoclonal antibody purification processes. J Chromatogr B Analyt Technol Biomed Life Sci. Mar. 15, 2007;848(1):64-78. Epub Jan. 16, 2007.
(Continued)

*Primary Examiner* — Joseph W Drodge
(74) *Attorney, Agent, or Firm* — Wolf, Greenfield & Sacks, P.C.

(57) ABSTRACT

The present invention provides a method and automated system for the purification of polypeptides including the direct filtration of solutions containing the polypeptides after purification.

9 Claims, 2 Drawing Sheets

(51) Int. Cl.
*C07K 1/36* (2006.01)
*B01D 15/08* (2006.01)
*G01N 30/02* (2006.01)
*G01N 33/68* (2006.01)
*B01D 61/20* (2006.01)
*B01D 61/22* (2006.01)
*B01D 61/16* (2006.01)

(52) U.S. Cl.
CPC .............. *C07K 1/36* (2013.01); *G01N 30/02* (2013.01); *G01N 33/68* (2013.01)

(58) Field of Classification Search
CPC ... C07K 1/18; C07K 1/20; C07K 1/22; C07K 1/34; C07K 1/36; B01D 15/08; B01D 15/10; B01D 15/26; B01D 15/38; B01D 36/00; B01D 37/04; B01D 61/00; B01D 61/02; B01D 61/04; B01D 61/10; B01D 61/12; B01D 61/14; B01D 61/16; B01D 61/20; B01D 61/22; B01D 65/02; B01D 65/022; B01D 2201/54; B01D 2311/04; B01D 2311/26; B01D 2311/2626; B01D 2311/2688
USPC ... 210/198.2, 656, 406, 416.1, 97, 109, 110, 210/143, 323.1, 650, 651, 652, 806; 422/70, 509, 513, 527, 534, 535; 435/6.1, 6.19, 7.1, 7.8, 283.1, 287.1, 435/287.7, 288.6, 308.1; 436/86, 87, 161, 436/177, 178; 530/333, 338, 344, 417
See application file for complete search history.

(56) References Cited

U.S. PATENT DOCUMENTS

| | | | |
|---|---|---|---|
| 4,980,130 A | 12/1990 | Metzger et al. | |
| 5,091,092 A * | 2/1992 | Newhouse | G01N 30/24 210/198.2 |
| 5,250,660 A * | 10/1993 | Shuman | C07K 5/06139 530/331 |
| 5,256,769 A * | 10/1993 | Kato | C07K 1/28 435/183 |
| 5,366,620 A * | 11/1994 | Schick | G01N 30/34 210/198.2 |
| 5,384,042 A * | 1/1995 | Afeyan | B01D 15/345 210/198.2 |
| 5,656,491 A | 8/1997 | Cassani et al. | |
| 5,705,610 A * | 1/1998 | Zuckermann | B01J 19/0046 530/333 |
| 5,906,747 A | 5/1999 | Coffman et al. | |
| 5,922,591 A | 7/1999 | Anderson et al. | |
| 6,168,948 B1 | 1/2001 | Anderson et al. | |
| 6,322,997 B1 * | 11/2001 | Blank | C07K 1/36 435/272 |
| 6,372,425 B1 * | 4/2002 | Arnold | C07K 16/1063 435/235.1 |
| 6,569,672 B1 | 5/2003 | Laugharn et al. | |
| 7,416,847 B1 | 8/2008 | Lindqvist et al. | |
| 8,906,231 B2 * | 12/2014 | Whickman | C07K 1/16 210/109 |
| 2003/0153729 A1 | 8/2003 | Duewel et al. | |
| 2004/0226884 A1 * | 11/2004 | O'Connor | B01L 3/5025 210/634 |
| 2005/0019902 A1 | 1/2005 | Mathies et al. | |
| 2007/0077239 A1 | 4/2007 | Tiruppathi et al. | |
| 2007/0144973 A1 * | 6/2007 | Tsonev | B01D 15/168 210/659 |
| 2008/0167450 A1 * | 7/2008 | Pan | C07K 16/065 530/387.3 |
| 2008/0233653 A1 * | 9/2008 | Hess | G01N 30/88 436/43 |
| 2008/0287661 A1 * | 11/2008 | Jones | B01L 3/0275 530/418 |
| 2012/0214974 A1 * | 8/2012 | Dawson | G01N 30/6052 530/395 |
| 2013/0041139 A1 * | 2/2013 | Brown | C07K 1/22 530/388.1 |

FOREIGN PATENT DOCUMENTS

| | | |
|---|---|---|
| JP | S62-26227 A | 2/1987 |
| JP | 2002-535968 A | 10/2002 |
| JP | 2003-064099 A | 3/2003 |
| JP | 2008-081503 A | 4/2008 |
| WO | WO 00/40613 A1 | 7/2000 |
| WO | WO 02/066099 A2 | 8/2002 |

OTHER PUBLICATIONS

Kanani et al., Reversible and irreversible membrane fouling during in-line microfiltration of concentrated protein solutions. Journal of Membrane Science. May 2008;315(1-2):1-10.

Rosenberg et al., Ultrafiltration concentration of monoclonal antibody solutions: Development of an optimized method minimizing aggregation. Journal of Membrane Science. Oct. 2009;342(1-2):50-9.

Valle et al., Biotechnology drugs: Integrated single-use technologies for biopharmaceuticals. Filtration & Separation. 2009;46(6):18-21.

Second Office Action for Chinese application No. 201510105706.9 dated Jan. 12, 2018.

Ho et al., Biotechnology and Biopharmaceutical; Transforming Proteins and Genes Into Drugs. Chemical Industry Press. Aug. 2005; pp. 56-57.

Introduction to Food Biotechnology. Chen, Daozong et al.; China Metrology Press, p. 184, published on Jan. 31, 2008.

\* cited by examiner

METHOD AND SYSTEM FOR POLYPEPTIDE PURIFICATION

RELATED APPLICATIONS

This application is a divisional of U.S. application Ser. No. 13/394,560, filed Jun. 19, 2012 and now pending, which is a national stage filing under 35 U.S.C. § 371 of international application PCT/EP2010/063295, filed Sep. 10, 2010, which was published under PCT Article 21(2) in English, the disclosures of which are incorporated by reference herein in their entireties.

FIELD OF THE INVENTION

The present invention relates to a method and automated system for the purification of polypeptides. In particular, the present invention relates to a Fast Protein Liquid Chromatography (FPLC) based method and respective automated system useful for the purification of polypeptides from complex mixtures.

BACKGROUND OF THE INVENTION

Fast Protein Liquid Chromatography (FPLC) is a form of liquid chromatography that is widely used, both in academia and industry, to separate and/or purify large quantities of various biomolecules such as proteins and DNA from complex mixtures. In FPLC a mixture containing soluble components, including the biomolecule of interest, is separated by passing it through a stationary phase with the aid of a liquid flow and the single components of the mixture are separated thereby. Depending on the elution method used, the components contained in the mixture migrate with different velocities through the stationary phase or are retained by the specific ligand interaction with the stationary phase thereby being separated from each other.

Due to its simple design, systems were developed automating FPLC. Automated FPLC based systems are inter alia manufactured by GE Healthcare, Chalfont St. Giles, United Kingdom, and marketed under the ÄKTA™ brand name.

Although simplifying the purification of biomolecules, purification cycles can only be set up to run on the current FPLC based systems where the produced flow-through or eluate containing the biomolecule of interest can be collected within a short time once it has left the system. Where the produced flow-through or eluate is not collected promptly, and thus, allowed to be exposed for a longer period, the risk of spoilage increases. Once there is spoilage in the flow-through or eluate the contained biomolecule is of no use and has to be disposed or alternatively extensively decontaminated which is time-consuming and costly. Thus, spoilage of the flow-through or eluate has to be avoided. Avoiding spoilage of the flow-through or eluate currently requires the attendance of operating personal at the time where the flow-through or eluate leaves the system, which increases, in particular for long-running cycles the amount of additional man hours for no increase in productivity. As a consequence, the running of purification cycles is set such that the time where the flow-through or eluate leaves the system falls within the regular working hours of the operating personal, which in turn restricts the timing and the number of purification cycles to be run.

BRIEF DESCRIPTION OF THE INVENTION

It is therefore an object of the present invention to provide means to overcome certain disadvantages of the current FPLC based systems. In particular, it is an object to provide a method and system with improved flexibility and/or productivity.

According to the present invention, this object is solved by the subject matter of the following items 1 to 23:

1. A Fast Protein Liquid Chromatography (FPLC) based method for purifying a polypeptide comprising the following steps:
    a) applying a liquid solution containing the polypeptide to a chromatographic means containing a stationary phase;
    b) separating the polypeptide from other molecules contained in the liquid solution by passing the liquid solution through the stationary phase of the chromatographic means;
    c) recovering the polypeptide from the chromatographic means in a flow-through or an eluate; and
    d) sterilizing the flow-through or eluate containing the recovered polypeptide by filtration.
2. The method according to item 1, wherein in step b) the polypeptide interacts with and is retained by the stationary phase; and in step c) the polypeptide is recovered by elution.
3. The method according to item 1 or 2, wherein in step d) the filtration is vacuum filtration.
4. The method according any one of items 1 to 3, wherein one or more of the steps a) to d) are automatically controlled.
5. The method according to any one of items 1 to 4, wherein the stationary phase is a biopolymer, inorganic polymer or synthetic polymer, each of which may optionally have functional groups coupled thereto, or is a membrane or monolith.
6. An automated Fast Protein Liquid Chromatography (FPLC) system configured for purifying a polypeptide according to the method of any one of items 1 to 5, comprising i) a chromatography module; and ii) a filtration module arranged after the chromatography module.
7. The system according to item 6, wherein the filtration module comprises at least one filtration means for sterile filtrating a flow-through or an eluate containing the polypeptide recovered from the chromatography module, and a control means for controlling the sterile filtration by the at least one filtration means.
8. The system according to item 6 or 7, wherein the filtration module comprises more than one filtration means for sterile filtrating a flow-through or an eluate containing the polypeptide recovered from the chromatography module, and for each filtration means a functionally connected control means for controlling the sterile filtration by the filtration means.
9. The system according to item 7 or 8, wherein the sterile filtration is driven by applying a vacuum.
10. The system according to any one of items 7-9, wherein the control means comprises at least one electrically powered relay, optionally comprising an input terminal and output terminal for control by a computing means, and at least one electromechanical valve, both functionally connected.
11. The system according to any one of items 7-10, wherein each control means comprises an electrically powered relay and an electromechanical valve, both functionally connected.
12. The system according to any one of items 7-11, wherein the control means comprises an input terminal and output terminal for control by a computing means.

13. The system according to any one of items 10-12, wherein the electromechanical valve is used to control the delivery of supply of vacuum to the filtration means.
14. The system according to any one of items 10-13, wherein the electromechanical valve is controlled by the electrically powered relay.
15. The system according to any one of items 10-14, wherein the electromechanical valve is a solenoid valve.
16. The system according to any one of items 6-15, wherein the filtration means is a filter cup.
17. The system according to any one of items 6-16, wherein filtration comprises four filtration and four control means.
18. A filtration module configured for the automated chromatography system according to any one of items 6-17, comprising at least one filtration means for sterile filtrating a solution containing a polypeptide and a control means for controlling the sterile filtration by the at least one filtration means.
19. The filtration module of item 18, comprising more than one filtration means for sterile filtrating a solution containing the polypeptide, and for each filtration means a functionally connected control means for controlling the sterile filtration by the filtration means.
20. The filtration module of item 18 or 19, wherein the filtration module comprises four filtration means and four control means, whereby always one filtration means is functionally connected with a control means.
21. A control means configured for the filtration module according to any one of items 18-20, comprising at least one electrically powered relay, optionally comprising an input terminal and output terminal for control by a computing means, and at least one electromechanical valve, both functionally connected.
22. The control means according to item 21, comprising more than one electrically powered relay, optionally comprising more than one input terminals and more than one output terminals for control by a computing system, and more than one electromechanical valves, both functionally connected.
23. The control means according to items 21 or 22, wherein the control means comprises four relays and four valves, whereby always one relay is functionally connected with one valve.

Directly sterilizing the flow-through or eluate once it has left the chromatographic means such as a purification column allows it and the biomolecule contained therein to be securely stored over a longer period without the risk of spoilage (i.e. using in-line sterile filtration carried out directly after chromatography). In this manner, the application is preferably directed to a device which comprises one chromatography module and subsequently a number of parallel filtration means (i.e. "more than 1"). The advantage of such a device is that the eluate formed after passing the chromatography module will run through a number of parallel filtration means which allows to filtrate a much greater volume of the liquid in a given time (compared to devices where one chromatography means is connected to only one filtration means). Due to the so obtained much quicker filtration the risk of spoilage of the proteins to be purified is greatly reduced.

Thus, the present method and system allows increased flexibility in timing the running of the cycles. Both elapsed time and man hours can be reduced by allowing unattended overnight cycling, thereby increasing the productivity of the system. Moreover, using vacuum filtration does not alter the system dynamics as would adding an inline filter driven by pressure. This allows a faster throughput where the system pressure limit is an issue.

DEFINITIONS

Figure 1:
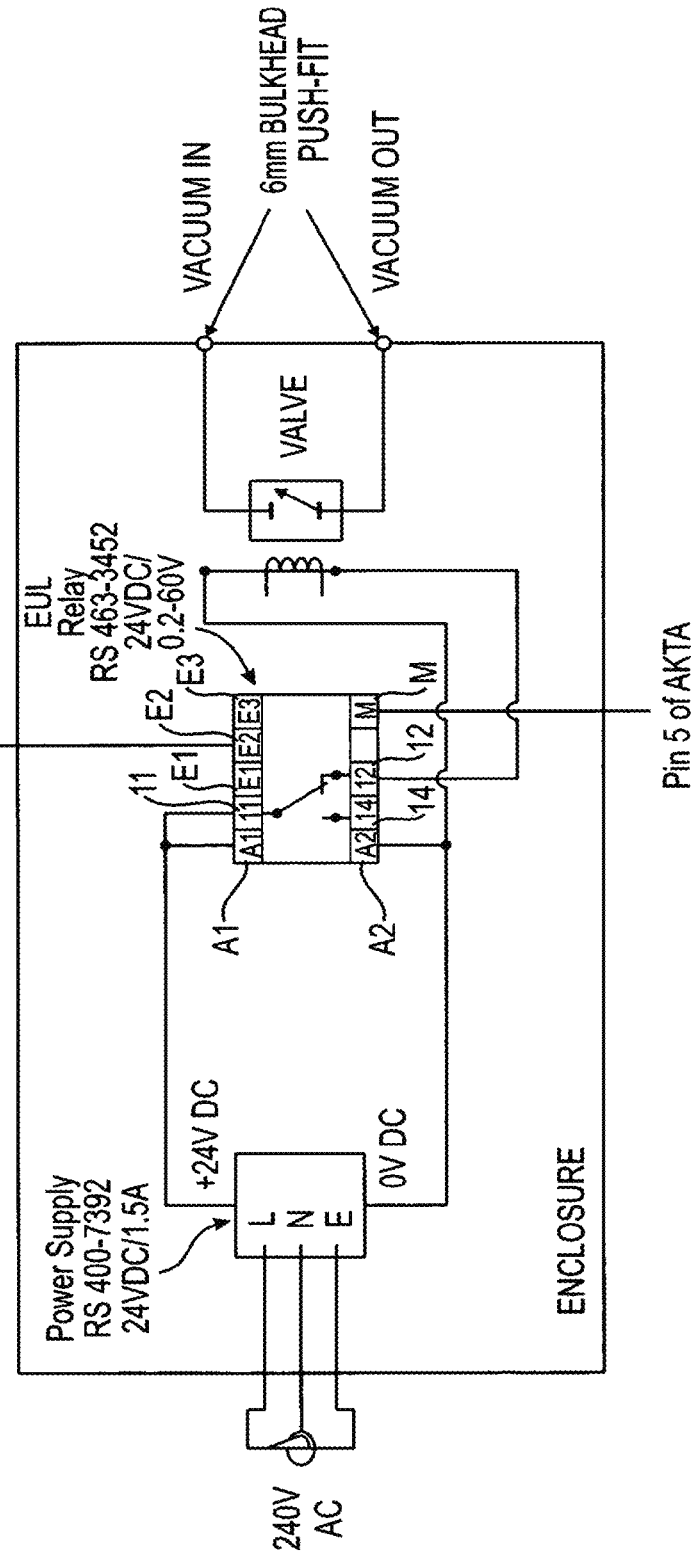
FIG. 1 is a schematic presentation of a control means of the present invention comprising one electrically powered EUL relay and one gas solenoid valve.

Unless specified otherwise herein, the terms "polypeptide" and "protein" refer to compounds formed from at least two amino acids. The "polypeptide" or "protein" may have catalytic or binding activity. The "polypeptide" or "protein" may be, for instance, but not limited to, an enzyme or antibody such as a domain or single domain antibody. For the purpose of the present invention, both terms may be used interchangeable.

Unless specified otherwise herein, the term "amino acid" encompasses any organic compound comprising at least one amino group and at least one acidic group. The amino acid can be a naturally occurring compound or be of synthetic origin. Preferably, the amino acid contains at least one primary amino group and/or at least one carboxylic acid group. The term "amino acid" also refers to residues contained in larger molecules such as peptides and proteins, which are derived from such amino acid compounds, and which are bonded to the adjacent residues by means of peptide bonds or peptidomimetic bonds.

Unless specified otherwise, the term "stationary phase" refers to a solid material which interacts with substances in a liquid solution.

Unless specified otherwise herein, the term "eluate" refers to a liquid which leaves a chromatographic means and has removed or dissolved away substances retained by a stationary phase from the stationary phase.

Unless specified otherwise herein, the term "flow-through" refers to a liquid which passes through and leaves a chromatographic means without removing or dissolving away substances retained by a stationary phase from the stationary phase.

Unless specified otherwise herein, the terms "to sterile filtrate" and "sterile filtration" refer to the elimination of contaminants such as microorganisms (e.g., bacteria, fungi etc.) from the flow-through or eluate. In the filtration process, the contaminants are retained by the filter, thereby separating the contaminants from the other component(s) contained in the flow-through or eluate.

DETAILED DESCRIPTION OF THE INVENTION

In one aspect, the present invention provides a FPLC based method for purifying a polypeptide. The method comprises the following steps:
  a) applying a liquid solution containing the polypeptide to a chromatographic means containing a stationary phase;
  b) separating the polypeptide from other molecules contained in the liquid solution by passing the liquid solution through the stationary phase of the chromatographic means;

c) recovering the polypeptide from the chromatographic means in a flow-through or an eluate; and d) sterilizing the flow-through or eluate containing the recovered polypeptide by filtration.

The chromatographic means, as used in the present invention, is a means usually employed in column chromatography, membrane chromatography or monolith chromatography for purifying polypeptides and proteins. Such means are well known in the art.

In some embodiments, the chromatographic means is a purification column. The purification column, as used in these embodiments, is a tube of variable size and inner diameter containing a stationary phase. Generally, the size and inner diameter of the tube ranges from 1 cm to 30 cm and 0.1 to 5 cm, respectively. However, the size of the tube may go up to 2 m. The tube may be made out of glass or metal such as stain-less steel. The purification column may be selected from commercially available purification columns such as, but not limited to, Tricorn™ columns, Mini-Beads™ columns, RESOURCE™ columns, HiTrap™ columns, HiLoad™ columns, HiPrep™ columns, Superdex™ columns and Superose™ columns. Alternatively, the purification column may be prepared in a laboratory setting by packing a stationary phase of choice into an empty column body. Examples of commercially available column bodies are the GE Healthcare XK series and the Millipore Vantage series.

The stationary phase is a solid filling material and may be a biopolymer, a synthetic polymer or an inorganic polymer. The biopolymer may be selected from cellulose, dextrane or agarose. The synthetic polymer may be selected from polyacrylamide, methacrylate or polyvinylbenzene/polystyrene. The inorganic polymer may be silica, hydroxyapatite or porous glass beads. Where appropriate, the filling material may further have coupled thereto functional groups which allow the specific interaction with the polypeptide. Such functional groups may be, but are not limited to, quaternary hydroxypropyl diethyl aminoethyl (QAE), quaternary trimethyl aminoethyl (Q), diethyl aminoethyl (DEAF), carboxymethyl (CM), sulfomethyl (S), sulfopropyl (SP). The functional group may also be a group specific or monospecific ligand such as a specific binding partner to the polypeptide of interest, e.g. an antigen in case of an antibody, or vice versa.

In other embodiments, the chromatographic means is a casing or column containing a membrane as the stationary phase. The column may be a tube as described above.

Membranes for use in chromatography are well known in the art. The membrane may be composed of one or more layers, for instance, but not limited to, two, three or four layers. The matrix material of the membrane may be, but not limited to, cellulose, modified cellulose, cross linked cellulose, nitrocellulose, polyamide such as Nylon, polyvinyl chloride (PVC) or polyvinylidene fluoride (PVDF).

In other embodiments, the chromatographic means is a casing or column containing a monolith as the stationary phase. The column may be a tube as described above.

Monoliths for use in chromatography are well known in the art.

In certain embodiments, the filtration in step d) is vacuum filtration.

In another aspect, the present invention provides an automated system for FPLC based methods. In particular, the invention provides an automated FPLC system configured for purifying a polypeptide according to the method detailed above. The system of the invention comprises a chromatography module and a filtration module. The filtration module is arranged after the chromatography module.

The chromatography module of the inventive system comprises a chromatographic means, a pump, a detection system and a control unit. In addition, the chromatography module of the invention may comprise an autosampler and/or a fraction collector. As a chromatography module an ÄKTA™ FPLC device manufactured and provided by GE Healthcare, Chalfont St. Giles, United Kingdom, may be used in the present invention.

The chromatographic means is as described above.

The pump allows for a constant flow of liquid through the system. The column chromatography module may comprise more than one pump, for instance, but not limited to, two, three or four pumps. The pump may be a peristaltic pump. The pump may also be a diaphragm, checked piston or lobe pump. The flow rate of the pump may range from 0.001 to 100 ml/min.

The detection system allows for the detection of the molecule(s) leaving the chromatographic means. The detection system may be a UV spectrophotometer. Alternatively, the detection system may also be a conductivity flow cell or a pH electrode.

The control unit allows for an automated control of each system component. The control unit may be a computing means executing a computer program which controls each system component. The computing means may be a personal computer having loaded thereon the computer program which is executed by the processor of the computer. The computing means may also be a network thin client. The computer program may be the UNICORN™ control software available from GE Healthcare, Chalfont St. Giles, United Kingdom. The UNICORN™ control software is preferred by the present invention.

The filtration module of the inventive system comprises at least one filtration means for sterile filtrating a flow-through or an eluate recovered from the chromatography module, and a control means for controlling the sterile filtration by the at least one filtration means. The filtration module may comprise more than one filtration means and/or more than one control means, for instance, but not limited to, two, three or four filtration means and/or two, three or four control means.

The filtration means allows the flow-through or eluate to be sterile filtrated, i.e. contaminants such as microorganisms are eliminated from the flow-through or eluate. The filtration means is a device containing a filter. In one embodiment of the invention, the filtration means is a filter cup, also referred to as vacuum driven bottle top filter. Filter cups are well known in the art. Using a filter cup allows the flow-through or eluate to be directly collected and subsequently sterile filtrated without the need of transfer. The pore size of the filter may be in the range of 0.45 to 0.1 µm, for instance, but not limited to 0.45 µm, 0.22 µm or 0.1 µm. It is generally expected that a pore size in the range of 0.45 to 0.1 µm retains microorganisms such as bacteria. In a particular embodiment, the pore size of the filter is 0.22 µm.

As detailed above, the sterile filtration may be driven by vacuum. In this case, a vacuum is supplied to the filtration means forcing the liquid and air through the filter by the application of negative pressure. This is achieved by supplying vacuum through a vacuum inlet on the filtration means located on the side of the filter opposite to the side holding the liquid to be filtrated. The vacuum is generated by a vacuum source which may be an on demand vacuum pump or piped vacuum pump. The filtration means and the vacuum source are connected via gas tubing and/or silicone laboratory tubing.

The control means of the invention allows controlling the sterile filtration by the filtration means. The control means comprises at least one electrically powered relay or solid state equivalent, and at least one electromechanical valve, both functionally connected. The electrically powered relay and the electromechanical valve are functionally connected via an electric circuit. The electric circuit may be composed of high input impedance voltage sensing relay, with hysteresis settings.

The control means may comprise more than one electrically powered relay and/or more than one electromechanical valve, for instance, but not limited to, two, three or four electrically powered relays and/or two, three or four electromechanical valves. In certain embodiments, the control means of the invention comprises an array of four relays.

The electrically powered relay may be a low powered relay. It may be powered by a dedicated 24V DC power supply unit, which may be installed in the same enclosure as the relay. In certain embodiments, the relay is powered by a 24V DC power supply.

The electrically powered relay is controlled by a control unit. The control unit may be a computing means executing a computer program which controls the switching of the relay. For control by a computing means, the electrically powered relay comprises an input terminal and an output terminal allowing the connection of the relay to the computing means. In certain embodiments, the electrically powered relay is controlled by the control unit of the chromatography module describe above.

In certain embodiments, the one or more electromechanical valves are solenoid valves. Solenoid valves are electromechanical valves for use with liquid or gas driven by running or stopping an electrical current through a solenoid, thereby opening or closing the valve. The solenoid may be a coil or wire. In particular embodiments, the solenoid valve is a gas solenoid valve.

In particular embodiments where vacuum filtration is performed, a gas solenoid valve is used to control the delivery of a supply of vacuum to a filtration means. In these embodiments, the gas solenoid is arranged between the filtration means and the vacuum source.

EXAMPLES

One example for the configuration of the control means is given in FIG. 1. The control means shown in FIG. 1 is constituted of a 24V DC power supply, a EUL relay and a gas solenoid valve within a single enclosure. The components are connected by electrical wiring. Via terminals E2 and M, the relay is connected to PIN 6 and PINI 5 of an ÄKTA™ purifier device, respectively. The gas solenoid valve is connected to terminals 11 and 12 of the EUL relay.

Figure 2:
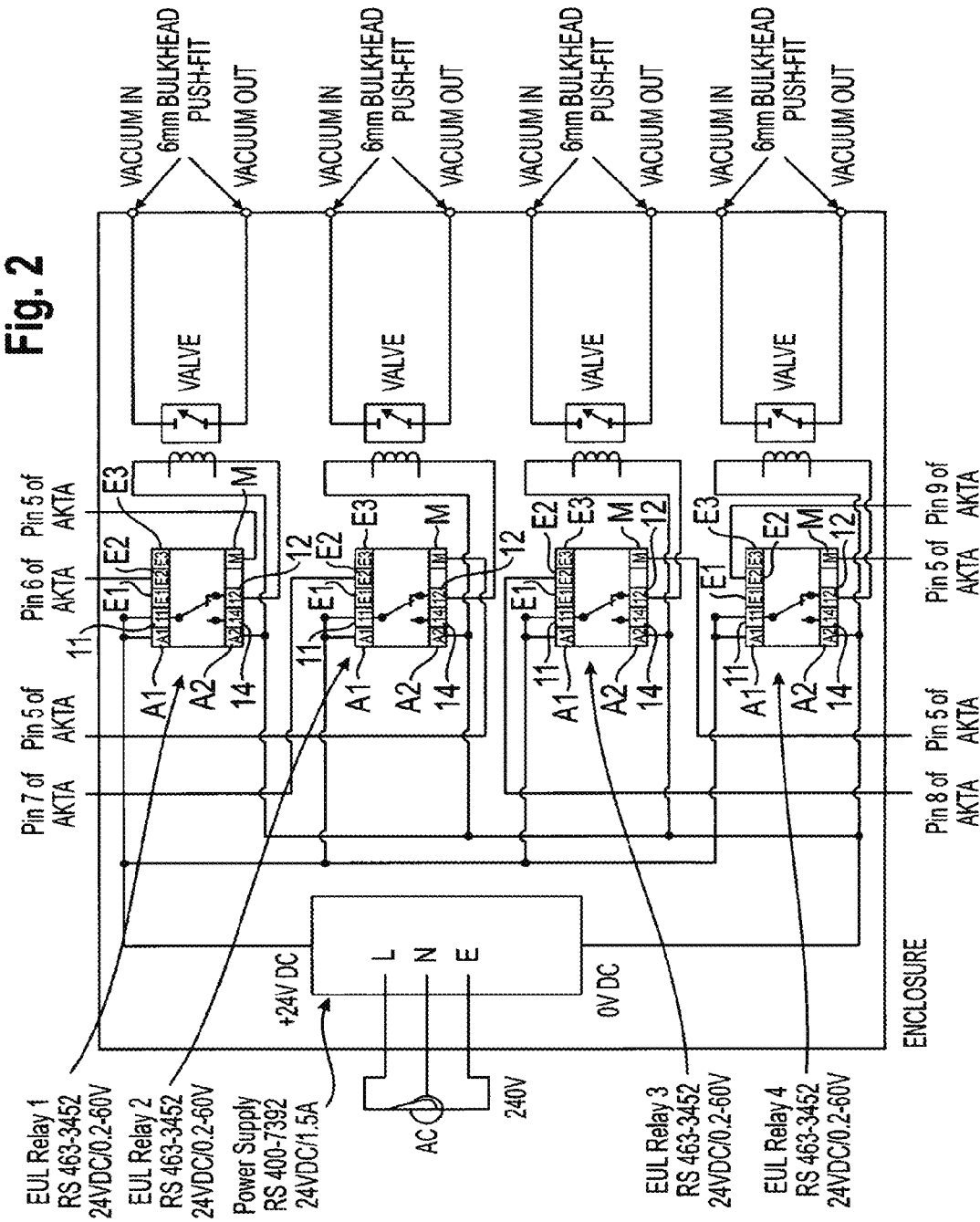
FIG. 2 is a schematic presentation of another control means of the present invention comprising an array of four electrically powered EUL relay and four gas solenoid valves.

A further example for the configuration of the control means is given in FIG. 2. The control means shown in FIG. 2 is constituted of a 24V DC power supply, four EUL relays and four gas solenoid valves within a single enclosure. The components are connected by electrical wiring. Each of the relays is connected via their terminal E2 to either PIN 6 PIN 7, PIN 8 or PIN 9 of an ÄKTA™ purifier device, while being connected to PIN 5 of the ÄKTA™ purifier device via terminal M. Each of the gas solenoid valves is connected to terminals and 12 of one of the EUL relays and is therefore independently controlled by the ÄKTA™ purifier device.

The above configurations allow the UNICORN™ control software to control the solenoid valves, and thus, the delivery of a supply of vacuum.

Both, the above-described filtration module as well as the control means encompassed therein represent further aspects of the present invention. According to these aspects, a filtration module and a control means are provided by the present invention which are configured for and thus to be used in an FPLC based system.

ÄKTA Vacuum Control Gadget

The purpose of the ÄKTA vacuum control gadget is to provide a method whereby the column eluate from an ÄKTA system can be sterilised without affecting system flow characteristics in a way that maintains product quality and integrity. This allows the ÄKTA system to be utilised for a greater proportion of the day as manual intervention requirements are reduced. To demonstrate the effect, a comparison of running with and without the gadget is provided.

Running without the Gadget

The system is set up at the beginning of the working day by the scientist. In this case a cycle is approximately 8 hours. After approximately 7 hours the scientist removes the eluate sample for analysis or further processing, and the system is allowed to complete its cycle. From this point onwards until the following morning the ÄKTA system sits idle.

If the ÄKTA was allowed to run unsupervised overnight 3 cycles could be completed. However, the output from the first cycle is held at ambient (room) temperature for 16 hours and the output from the second cycle is held at ambient temperature for 8 hours. The ÄKTA is not a sterile system and bio burden from the system or from laboratory air is introduced. High protein solutions encourage microbial growth which affect spoilage of the collected sample, resulting in negative impact on downstream analysis or further processing.

Running with the Gadget

The following example was performed using the ÄKTA purifier system. The system is set up at the beginning of the working day by the scientist. Sufficient materials are provided to allow the machine to carry out 3 cycles of approximately 8 hours each. After seven hours the system has collected the output from cycle one and sterilises it under the control of the gadget. After fifteen hours the eluate from the second cycle is likewise sterilised, followed by the third cycle after 23 hours. The eluate from the first cycle is held for 16 hours at ambient temperature but there are no microbial growth as any introduced microbes are removed by the sterilising filter, likewise for the second cycle.

SUMMARY

Operating without the gadget restricts the ÄKTA to produce material only within the working day. Attempting to run the machine outside of the working day places the product samples generated at risk of contamination and damage by microbial growth.

Running with the gadget allows maximum utilisation to be made of the automated chromatography system without the risk of microbial growth.

Having thus described several aspects of the invention, it is to be understood that the spirit and scope of the invention covers all possible combinations of the above-described embodiments. Furthermore, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A Fast Protein Liquid Chromatography (FPLC) based method for purifying a polypeptide comprising the following steps:
   a) applying a liquid solution containing the polypeptide to a chromatographic module comprising a stationary phase and an outlet;
   b) separating the polypeptide from other molecules contained in the liquid solution by passing the liquid solution through the stationary phase of the chromatographic module;
   c) recovering the polypeptide from the chromatographic module in a flow-through or an eluate; and
   d) sterilizing the flow-through or eluate containing the recovered polypeptide by in-line sterile filtration using at least one in-line filtration module comprising an inlet and which is arranged directly after the chromatography module, wherein the outlet of the chromatography module is connected to the inlet of the at least one in-line filtration module; wherein the at least one in-line filtration module is driven by vacuum from a vacuum source for sterile filtrating a flow-through or an eluate containing the polypeptide recovered from the chromatography module; wherein the in-line filtration module comprises a filter with a pore size of 0.45 to 0.1 µM.

2. The method according to claim 1, wherein in step b) the polypeptide interacts with and is retained by the stationary phase; and in step c) the polypeptide is recovered by elution.

3. The method according to claim 2, wherein one or more of the steps a) to d) are automatically controlled.

4. The method according to claim 3, wherein the stationary phase is a biopolymer, inorganic polymer or synthetic polymer, each of which may optionally have functional groups coupled thereto, or is a membrane or monolith.

5. The method according to claim 2, wherein the stationary phase is a biopolymer, inorganic polymer or synthetic polymer, each of which may optionally have functional groups coupled thereto, or is a membrane or monolith.

6. The method according to claim 1, wherein one or more of the steps a) to d) are automatically controlled.

7. The method according to claim 6, wherein the stationary phase is a biopolymer, inorganic polymer or synthetic polymer, each of which may optionally have functional groups coupled thereto, or is a membrane or monolith.

8. The method according to claim 1, wherein the stationary phase is a biopolymer, inorganic polymer or synthetic polymer, each of which may optionally have functional groups coupled thereto, or is a membrane or monolith.

9. The method according to claim 1, wherein the at least one in-line filtration module comprises more than one filter for parallel filtration.

* * * * *